US012791642B2

(12) United States Patent
Bollenbeck et al.

(10) Patent No.: US 12,791,642 B2
(45) Date of Patent: Nov. 10, 2026

(54) DOUBLE-RESONANCE MRT LOCAL COIL WITH INTEGRATED PILOT TONE SIGNAL FREQUENCY CONVERTER

(71) Applicant: Siemens Healthineers AG, Forchheim (DE)

(72) Inventors: Jan Bollenbeck, Eggolsheim (DE); Peter Speier, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 155 days.

(21) Appl. No.: 18/775,400

(22) Filed: Jul. 17, 2024

(65) Prior Publication Data

US 2025/0035723 A1 Jan. 30, 2025

(30) Foreign Application Priority Data

Jul. 28, 2023 (EP) ..................................... 23188387

(51) Int. Cl.
*G01V 3/00* (2006.01)
*G01R 33/36* (2006.01)
*A61B 5/055* (2006.01)

(52) U.S. Cl.
CPC ..... *G01R 33/3692* (2013.01); *G01R 33/3621* (2013.01); *A61B 5/055* (2013.01)

(58) Field of Classification Search
CPC .. G01R 33/3692; G01R 33/3621; A61B 5/055
USPC .......................................................... 324/318
See application file for complete search history.

(56) References Cited

U.S. PATENT DOCUMENTS

| | | | | |
|---|---|---|---|---|
| 7,123,009 | B1 | 10/2006 | Scott | |
| 10,928,477 | B2 | 2/2021 | Speier | |
| 2010/0112614 | A1* | 5/2010 | Axelrod | C12Q 1/54 |
| 2015/0320342 | A1 | 11/2015 | Biber | |
| 2024/0133988 | A1 | 4/2024 | Lustig | |

FOREIGN PATENT DOCUMENTS

| | | | | |
|---|---|---|---|---|
| CN | 112083367 | A * | 12/2020 | A61B 5/7203 |
| DE | 102014219092 | A1 * | 3/2016 | G01D 5/2291 |
| DE | 102018220351 | A1 * | 5/2020 | G01R 33/5673 |
| DE | 202023103471 | U1 | 7/2023 | |
| EP | 3895610 | A1 * | 10/2021 | G01S 13/50 |
| WO | WO-2005024448 | A1 * | 3/2005 | G01R 33/54 |
| WO | 2022178050 | A1 | 8/2022 | |

OTHER PUBLICATIONS

Anand, Suma, and Michael Lustig. "Beat pilot tone: versatile, contact-free motion sensing in MRI with radio frequency intermodulation." arXiv preprint arXiv:2306.10236 (2023). 1-16.

(Continued)

*Primary Examiner* — Walter L Lindsay, Jr.
*Assistant Examiner* — Frederick Wenderoth
(74) *Attorney, Agent, or Firm* — Lempia Summerfield Katz LLC

(57) ABSTRACT

A local coil for a magnetic resonance tomography is designed to acquire a magnetic resonance signal and a pilot tone signal and to forward them to a receiver of the magnetic resonance tomography system for evaluation. The pilot tone signal lies in a first frequency range and the magnetic resonance signal in a second frequency range.

17 Claims, 4 Drawing Sheets

(56) References Cited

OTHER PUBLICATIONS

Choi, Chang-Hoon, et al. "The state-of-the-art and emerging design approaches of double-tuned RF coils for X-nuclei, brain MR imaging and spectroscopy: A review." Magnetic resonance imaging 72 (2020): 103-116.
Griffiths, H., W. R. Stewart, and W. Gough. "Magnetic induction tomography: a measuring system for biological tissues." Annals of the New York Academy of Sciences 873.1 (1999): 335-345.
Gruber, Bernhard, et al. "RF coils: A practical guide for nonphysicists." Journal of magnetic resonance imaging 48.3 (2018): 590-604.

* cited by examiner

DOUBLE-RESONANCE MRT LOCAL COIL WITH INTEGRATED PILOT TONE SIGNAL FREQUENCY CONVERTER

RELATED APPLICATION

This application claims the benefit of EP 23188387.7, filed on Jul. 28, 2023, which is hereby incorporated by reference in its entirety.

FIELD

Independent of the grammatical term usage, individuals with male, female or other gender identities are included within the term.

The disclosure relates to a local coil for receipt of a pilot tone signal and to a magnetic resonance tomography system with a local coil. The magnetic resonance system has a receiver designed simultaneously to receive and evaluate a pilot tone signal and a magnetic resonance signal, which is supplied to it by the local coil.

BACKGROUND

Magnetic resonance Tomography (MRT) systems are imaging devices, which, in order to map an object under examination, align nuclear spins of the object under examination with a strong external magnetic field and use a magnetic alternating field to excite them to precession about this alignment. The precession or return of the spins from this excited state into a state with less energy in turn generates in response a Magnetic alternating field which is received via antennas.

With the help of magnetic gradient fields, a position encoding is impressed on the signals, and subsequently enables the received signal to be assigned to a volume element. The received magnetic resonance signal is then evaluated and a two- or three-dimensional imaging representation of the object under examination is provided.

The magnetic resonance signals are very weak. To obtain a sufficiently high signal-to-noise ratio, the signal must hence be captured over a long time, in one or in repeated scans. The capture of the magnetic resonance signals is in this case slow compared to unavoidable movements of the patient such as heartbeat or respiratory motion. The movements in this case cause artifacts in the generated images.

Nevertheless, it is possible to map the moving organs if a short image capture is performed repeatedly in synchronization with the movement and averages over the captured data.

A synchronization can be carried out with dedicated sensors, such as for example a respiratory belt or EKG electrodes.

To obviate these additional sensors, it is also already known from the printed publication US 2015/0320342 A1 to couple a continuous, mono-frequency magnetic alternating field, originating from a small conductor loop, at least partially through the body of the patient into the individual elements of a magnetic resonance local coil.

Since most biological tissues are almost completely transparent to magnetic fields, the generated magnetic field penetrates the body of the patient almost unchanged. However, most tissues are (weakly) conductive and hence the continuous wave magnetic field induces eddy currents. These eddy currents then in turn generate a magnetic field superimposed on the excitation field, resulting in modulations in the received magnetic field in the receiving coil.

By evaluating this signal, it is possible to infer a movement phase of the heart or of respiration.

The complexity of hardware is reduced if, in order to capture the movement, a signal is used which has a frequency close to the frequency of the magnetic resonance signal and thus can be evaluated with the same receiver, preferably simultaneously. However, for movements of the heart in particular, the degree of modulation decreases strongly with frequency, so that in magnetic resonance systems for low static magnetic field strengths B0, for example of 0.5 T, a reliable detection of the heartbeat is scarcely possible in this way.

SUMMARY AND DESCRIPTION

It is hence an object to make the capture of movements of the patient better and more reliable in the case of low-field systems.

The object is achieved by a local coil and a magnetic resonance tomography system.

The local coil is intended for use with a magnetic resonance tomography system, in order to acquire magnetic resonance signals of a patient or object in a static magnetic field B0 of the magnetic resonance tomography system. The frequency of the magnetic resonance signal is defined by the magnetic field strength B0 and a magnetic moment of the nuclear spins to be captured and is referred to as the Larmor frequency.

The local coil is in particular designed to acquire a magnetic resonance signal and a pilot tone signal and to forward them to a receiver of the magnetic resonance tomography system for evaluation. Acquisition in this case, in particular, refers to the conversion of the magnetic or electromagnetic radio-frequency alternating field of the nuclear spins and of the pilot tone signal into an electrical signal by an antenna or induction loop. Pilot tone signal means a magnetic or electromagnetic radio-frequency signal that is emitted by a pilot tone signal transmitter, preferably integrated into the local coil, and interacts with the patient so that the patient's movements such as respiratory motion or heartbeat are used to modulate the pilot tone to form a pilot tone signal. The acquisition can also include further signal processing steps such as amplification or filtering.

The pilot tone and thus the pilot tone signal that is acquired by the antenna or induction loop lie in a first frequency range, wherein frequency range means a spectral range which includes the frequency of the pilot tone and at least sidebands caused by the modulation. The first frequency range can include a bandwidth of more than 10 Hz, 100 Hz, 1 kHz, 10 kHz or even 100 kHz.

The magnetic resonance signal acquired by the antenna or induction loop lies in a second frequency range which includes the already defined Larmor frequency of the magnetic resonance tomography system with which the local coil is used. The bandwidth of the second frequency range is substantially specified by the bandwidth of the magnetic resonance signals, which in turn depends on layer thicknesses to be captured and magnetic field strengths of gradients for position encoding. A bandwidth of the second frequency range can include more than 100 kHz, 50 kHz, 1 MHz or 5 MHz. The processed magnetic resonance signal or if applicable also the frequency-converted magnetic resonance signal is also referred to as such below.

The first frequency range and the second frequency range are in this case disjunct. A signal which is in the first frequency range is not part of the second frequency range and vice versa. As set out below with regard to the subclaims, it is in particular also conceivable for a frequency in the first frequency range to be an integral multiple of a frequency in the second frequency range. The frequency ranges have a frequency spacing which is significant compared to for example a center frequency or a bandwidth of one of the frequency ranges, for example greater than an integral multiple where n>1 thereof.

The local coil has a frequency converter. A frequency converter is a device that converts a signal from one frequency to another. A frequency converter can for example be realized by a mixer that converts a first signal with a first frequency to one or more other frequencies by mixing, e.g., by multiplication or another non-linear operation.

In accordance with an implementation, the frequency converter of the local coil converts the acquired pilot tone signal into a common frequency range with the magnetic resonance signal.

To this end, it is firstly conceivable for a first frequency converter to convert the pilot tone signal into the frequency range into which the magnetic resonance signal emitted by the nuclear spins also falls, in other words the common frequency range is the second frequency range.

However, it is also conceivable for the first frequency converter to convert the pilot tone signal into a common frequency range which is disjunct to the first frequency range and the second frequency range. The magnetic resonance signal captured by the antenna is converted into the common frequency range by a second frequency converter or else by the first frequency converter. This can for example be an intermediate frequency which prevents feedback effects to the input signal, reduces the attenuation during the transmission to the magnetic resonance tomography system, and/or serves a frequency multiplex.

In other words, the pilot tone signal is converted from the first frequency range into a common frequency range with the magnetic resonance signal, so that the converted pilot tone signal can then be processed and evaluated by a receiver for the magnetic resonance signal.

The frequency conversion is preferably carried out such that the magnetic resonance signal and the converted pilot tone signal do not overlap in the second frequency range but lie next to one another. This can be achieved for example by a suitable selection of the frequency of a mixed signal or of an oscillator signal.

The frequency converter of the local coil advantageously enables the pilot tone signal to have a significantly higher frequency than the magnetic resonance signal and nevertheless to be capable of being processed by a receiver for the magnetic resonance signal. In particular, in magnetic resonance tomography systems with a low static magnetic field, a pilot tone solution with high movement sensitivity can be provided inexpensively in this way.

Further advantageous implementations are explained with regard to the subclaims.

In one conceivable form, the local coil has an input for an oscillator signal. An oscillator signal should be understood as a signal which specifies a reference frequency that is preferably highly constant. The oscillator signal can for example be an analog sine signal which is transmitted electrically via a current or voltage modulation. Also conceivable is the modulation of a carrier wave, for example for a wireless transmission via radio wave, optically or by induction by a modulated magnetic field. The input can correspondingly be an electrical or optical input, an antenna, or an induction loop. Also possible is a digital transmission by encoding on a corresponding carrier signal.

The local coil is in this case designed to generate a pilot tone from the oscillator signal, for transmission or coupling. It is for example conceivable for the oscillator signal to be converted or multiplied to a different frequency by a frequency converter. However, it is also conceivable for the oscillator signal additionally or only to be amplified and/or filtered.

The local coil is further designed to generate a mixer signal from the oscillator signal for the frequency conversion of the pilot tone signal using the frequency converter, or to derive it therefrom. If the pilot tone is generated by frequency multiplication, the mixer signal can likewise be generated from the oscillator signal by frequency multiplication. However, it is also conceivable for the oscillator signal to have a high frequency, for example higher than the mixer signal and/or the pilot tone, so that mixer signal and/or pilot tone are generated by frequency division. Some particularly advantageous combinations are explained in greater detail below. Frequency multiplication is in this case regarded as a multiplication by integral factors, as is achieved for example by harmonic waves or harmonics, but also by rational factors, as can be realized for example by synthesizers or PLLs.

The generation of both pilot tone and mixer signal from a common, supplied oscillator signal advantageously results in high frequency stability and phase synchronization of the pilot tone signal and thus also in the avoidance of disturbances in the magnetic resonance image.

In one possible implementation of the local coil, the local coil has a first frequency multiplier with a first multiplication factor m to generate the pilot tone from the oscillator signal and a second frequency multiplier with a second multiplication factor n to generate the mixer signal from the oscillator signal. In other words, the frequency of the pilot tone is an m-fold multiple of the frequency of the oscillator signal and the frequency of the mixer signal is an n-fold multiple of the frequency of the oscillator signal.

Both the pilot tone and the mixer signal for mixing down the pilot tone signal are advantageously generated from a single oscillator signal, thereby simplifying the frequency scheme and reducing possible sources of interference for the magnetic resonance signal.

In a preferred implementation of the local coil, the difference between the first multiplication factor m and the second multiplication factor n is 1. In other words, the absolute value of the difference (n−m) is equal to 1. In this case m and n are preferably natural numbers greater than 1, but it is also conceivable for one of them to have the value 1.

A frequency multiplication with the aforementioned numerical ratios advantageously means that at least one of the mixed products again has the frequency of the oscillator signal in a stable manner, thereby reducing or avoiding image artifacts by interference signals in the form of mixed products with further frequency values and enables processing by a receiver for the magnetic resonance signal.

In one conceivable implementation of the local coil, the mixer signal has the same frequency as the oscillator signal. In other words, the oscillator signal is not changed in frequency by division, multiplication or mixing before it is used as a mixer signal. The frequency converter to which the mixer signal is supplied is a switching mixer. The term switching mixer should in this case be understood to mean a mixer which does not carry out an analog multiplication of both the signals to be mixed, but the polarity of the frequency to be mixed is switched by the mixer frequency in a controlled manner. It is also possible to switch on and off instead of switching the polarity. The mixer signal is in this case preferably a symmetrical square-wave signal, i.e., with period durations of equal length for both states.

Due to the Fourier equivalence, a switching mixer advantageously acts like an analog mixer with a mixer signal consisting of a Fourier series with odd multiples of the fundamental frequency as components. Thus, it is possible to dispense with a separate frequency converter to generate the mixer signal from the oscillator signal. The reduced mixer conversion gain for the pilot tone signal due to the lesser amplitude of the mixer signal harmonics can be compensated for by a corresponding gain or frequency dependency of the subsequent signal processing.

In one possible implementation of the local coil, the local coil has an antenna coil to receive the pilot tone signal and the magnetic resonance signal. In other words, the local coil is designed to acquire the pilot tone signal and the magnetic resonance signal simultaneously with an antenna coil, with signal levels which permit an evaluation in the form of imaging and movement detection. To this end, the antenna coil simultaneously has a resonance in the first frequency range and the second frequency range, in other words for the pilot tone signal and the magnetic resonance signal.

Advantageously, in this way, separate antenna coils are not required for magnetic resonance signals and pilot tone signals with significantly different frequencies, thereby reducing space and effort for detuning.

In one conceivable implementation of the local coil, the local coil has an attenuator. An attenuator is regarded as an electronic component or a circuit that has a signal input and a signal output, wherein the attenuator outputs a signal applied to the signal input at at least one predetermined frequency reduced in level by a predetermined attenuation factor at the signal output. The attenuator is designed to attenuate the pilot tone signal to a level comparable to or lower than the magnetic resonance signal to be received, before it is forwarded to the magnetic resonance tomography system to be evaluated jointly with the magnetic resonance signal. Comparable should be understood to mean that the level of the pilot tone signal downstream of the attenuator is equal to or below a level of the received magnetic resonance signal, in particular a maximum magnetic resonance signal to be received, which is defined by an upper limit of the linear amplification range of an input amplifier of the receiver of the magnetic resonance tomography system. The attenuation of the received pilot tone signal compared to the received magnetic resonance signal by the attenuator is preferably greater than 3 dB, 6 dB or 9 dB. However, the attenuation is preferably also not greater than 12 dB, 18 dB or 24 dB.

The attenuator for the pilot tone signal is in this case preferably arranged upstream of the frequency conversion in the signal path of the pilot tone signal but can also be arranged downstream of the frequency conversion in the signal path of the pilot tone signal or can also be part of the frequency conversion.

In one implementation of the local coil with a plurality of antenna coils in an antenna matrix, it is in this case conceivable that due to the different distances of the antenna coils from a transmission antenna or induction loop for the pilot tone, integrated into the local coil, the attenuation for the attenuator for the pilot tone is designed differently for the individual signal paths assigned to the antenna coils. The attenuation would preferably decrease with increasing distance of the antenna coil from the transmission antenna because of the lower expected level of the pilot tone signal. It is also conceivable for the attenuator to be adjustable by a controller of a magnetic resonance tomography system, in order for example to be able to take account of different arrangements in the case of a flexible local coil matrix.

The attenuator in combination with the large frequency spacing of the pilot tone signal from the Larmor frequency advantageously allows only the pilot tone signal to be attenuated compared to the magnetic resonance signal. Thus, the pilot tone signal can be transmitted with a significantly higher level, and the SNR for the evaluation of the pilot tone signal can be improved. Thus, the detection of movements such as for example heartbeat or respiratory motion takes place more stably and more reliably.

In one possible implementation of the local coil, the local coil is designed to transmit the pilot tone with a higher level than the magnetic resonance signal to be received. In other words, because of the frequency spacing between Larmor frequency and the pilot tone, its level can advantageously be greater than that of a magnetic resonance signal to be received, without interfering with its receipt.

Thus, the SNR of the pilot tone signal can be improved, and the movement detection can be improved by the pilot tone, in particular more stably and more reliably.

In one conceivable implementation of the magnetic resonance tomography system, the magnetic resonance tomography system has a local coil, as well as an oscillator and a receiver. The magnetic resonance tomography system is designed, with the oscillator of the local coil, to provide the oscillator signal. This relates, in particular, to the choice of the frequency and the stability thereof. The oscillator signal and the mixer signal or mixer signals derived therefrom must firstly be suitable for converting the magnetic resonance signals and/or pilot tone signals to the desired frequencies or intermediate frequencies and must be simultaneously selected so that corresponding mixed products and harmonic waves do not interfere with the received magnetic resonance signals and intermediate frequencies. In addition, the receiver is designed to evaluate the pilot tone signal and the magnetic resonance signal that it obtains from the local coil, for image capture and movement detection. In particular, the oscillator signal and the frequency converter and mixer are designed such that they fall in a common frequency range that can be evaluated by the receiver. A detailed example of a suitable frequency scheme is explained with respect to the figures.

BRIEF DESCRIPTION OF THE DRAWINGS

The above-described properties, features and advantages of this invention and the manner in which they are achieved will become clearer and more readily understandable in connection with the following description of the exemplary embodiments, which are explained in greater detail in connection with the drawings, in which.

DETAILED DESCRIPTION

Figure 1:
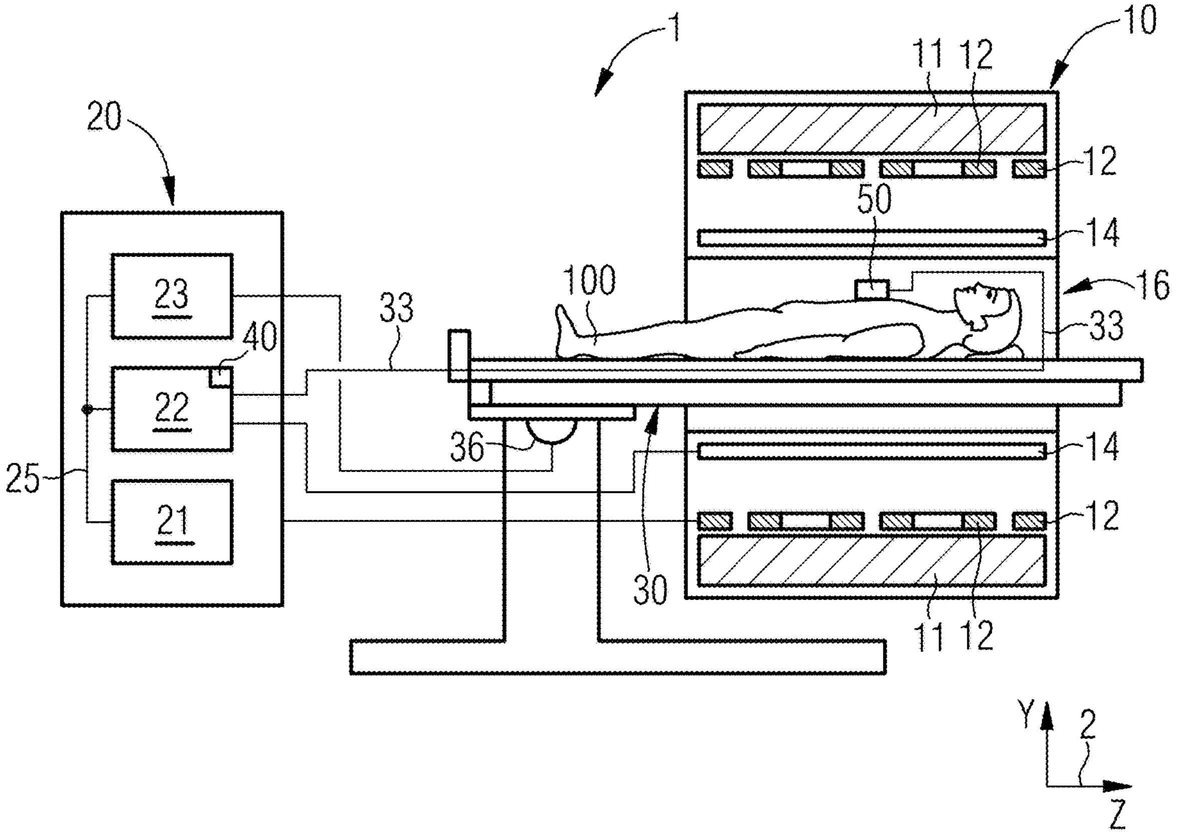
FIG. 1 shows a schematic representation of an example magnetic resonance system.

FIG. 1 shows a schematic representation of a form of embodiment of a magnetic resonance system 1.

The magnet unit 10 has a field magnet 11 which generates a static magnetic field B0 for the alignment of nuclear spins of samples or of the patient 100 in an acquisition area. The acquisition area is characterized by an extremely homogeneous static magnetic field B0, wherein the homogeneity, in particular, relates to the magnetic field strength or the orientation and the absolute value. The acquisition area is virtually spherical and is arranged in a patient tunnel 16 which extends in a longitudinal direction 2 through the magnet unit 10. A patient couch 30 can be moved in the patient tunnel 16 by the positioning unit 36. The field magnet 11 is usually a superconducting magnet that can provide magnetic fields with a magnetic flux density of up to 3 T, and even higher in the latest devices. However, permanent magnets or electromagnets with normally conducting coils can also be used for lower field strengths.

Furthermore, the magnet unit 10 has gradient coils 12 which are designed to superimpose variable magnetic fields on the magnetic field B0 in three spatial directions for the spatial differentiation of the captured mapping areas in the examination volume. The gradient coils 12 are usually coils made of normally conducting wires that can generate fields orthogonal to one another in the examination volume.

The magnet unit 10 likewise has a body coil 14 designed to radiate a radio-frequency signal supplied via a signal line into the examination volume and to receive resonance signals emitted by the patient 100 and to emit them via a signal line.

A control unit (controller) 20 supplies the magnet unit 10 with the various signals for the gradient coils 12 and the body coil 14 and evaluates the received signals.

Thus, the control unit 20 has a gradient controller 21 which is designed to supply the gradient coils 12 with variable currents, via supply lines, which provide the desired gradient fields in the examination volume in a time-coordinated manner.

Furthermore, the control unit 20 has a radio-frequency unit (generator or transmitter) 22 which is designed to generate a radio-frequency pulse with a specified temporal characteristic, amplitude and spectral power distribution for the excitation of a magnetic resonance of the nuclear spins in the patient 100. In this case, pulse powers in the kilowatt range can be achieved. The excitation pulses can be radiated into the patient 100 via the body coil 14 or else via a local transmission antenna.

The radio-frequency unit 22 also has a receiver 40 to receive or preprocess a magnetic resonance signal from the patient 100, which is acquired by the local coil 50 and transmitted to the receiver 40 via a signal connection. The receiver 40 is additionally designed to receive and evaluate a pilot tone.

In one implementation, the radio-frequency unit 22 also has a pilot tone transmitter 70 which transmits a pilot tone to a pilot tone transmission antenna or coupling loop, possibly also in the local coil 50, for coupling out via a signal connection. However, a separate pilot tone transmitter 70 which acts independently of the magnetic resonance system 1 is also conceivable.

A controller 23 communicates with the gradient controller 21 and the radio-frequency unit 22 via a signal bus 25.

A local coil 50 is arranged on the patient 100*a* and is connected to the radio-frequency unit 22 and its receiver via a connection cable 33.

The local coil 50 preferably further has a pilot tone transmission antenna or coupling loop, with which a pilot tone can be transmitted or induced into the body of the patient 100. The pilot tone is preferably generated by the coupling loop in the form of a magnetic alternating field, which at least partially penetrates the body of the patient 100 and couples into the antenna coils 51 of the magnetic resonance tomography system 1.

Figure 2:
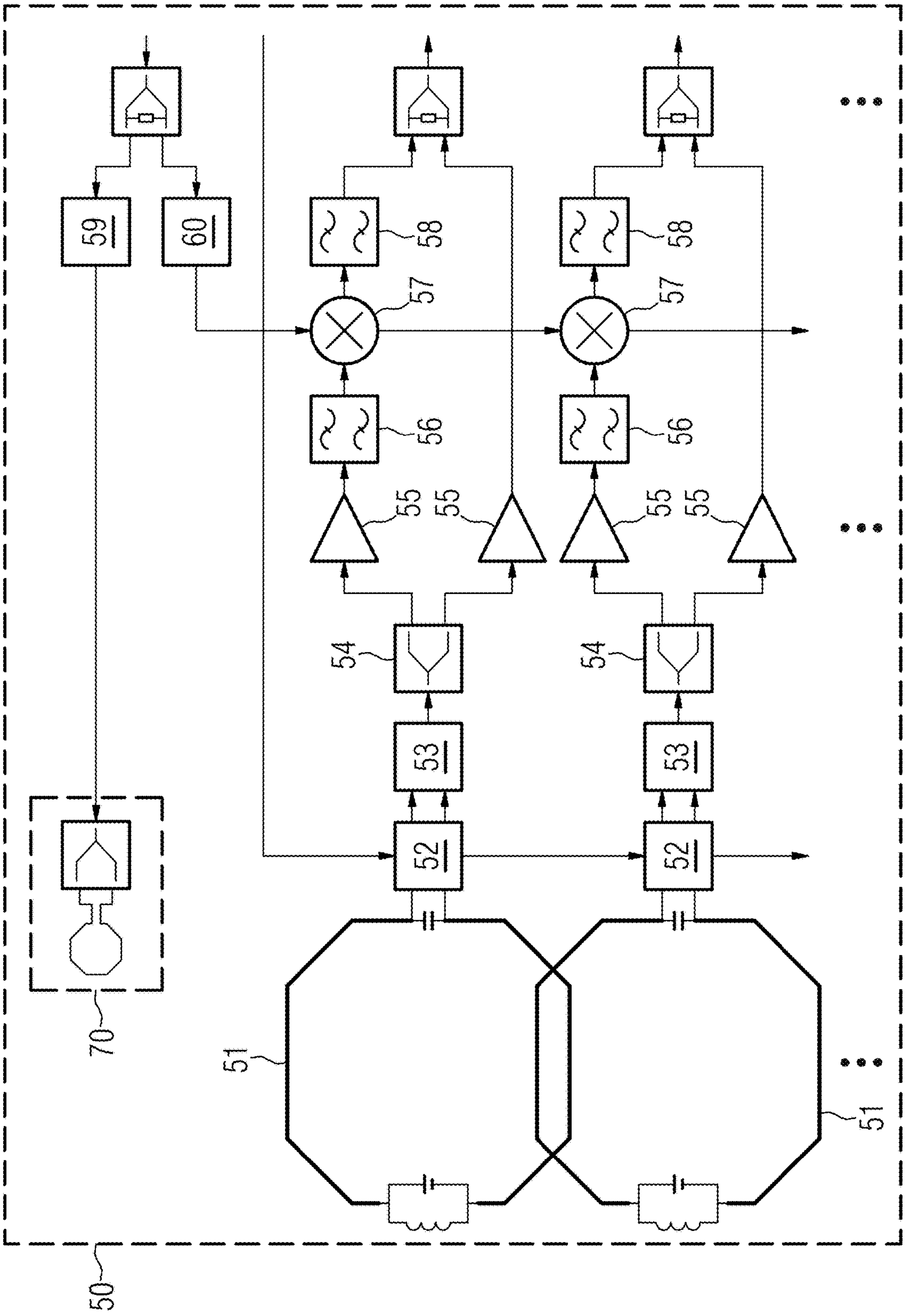
FIG. 2 shows a schematic representation of an exemplary local coil.

FIG. 2 shows a schematic representation of an exemplary implementation a local coil 50.

The local coil 50 has a plurality of antenna coils 51. The antenna coils 51 are designed for the receipt of both the magnetic resonance signal and the pilot tone signal with significantly different frequencies. In order to achieve as high a sensitivity as possible at both frequencies, the antenna coils 51 are double-resonant at these frequencies. This can for example be achieved, as shown in FIG. 2, by a parallel-resonance circuit, which is connected into the loop of the antenna coil 51.

The antenna coils 51 are further connected to a detuning device 52 which detunes the antenna coil 51, in order to protect it during the excitation pulse.

A subsequent matching circuit 53 ensures impedance matching of the antenna coil 51 to the subsequent signal processing. The matching circuit 53 can in this case have, as in FIG. 2, the function of an unbalancer, the transition from the symmetrical antenna signal to symmetrical amplifier input.

In a diplexer 54, the pilot tone signal and the magnetic resonance signal are separated on the basis of their different frequencies and are then amplified in preamplifiers or LNA 55. In a first filter 56, the pilot tone signal is then filtered, in order to avoid undesired frequency components in the subsequent mixing down in the mixer 57. The mixed product is then, in a second filter 58, restricted to the frequency band of the magnetic resonance signals, so that it can be transmitted together with the magnetic resonance signal and can be evaluated by the receiver 40. The generation of the mixed frequencies and an exemplary frequency scheme are shown below.

The order of the individual processing steps can also be partially transposed, in particular for linear processing steps. It is also conceivable for functions to be combined, for example matching and filtering.

In particular, it is also conceivable for an attenuator to be provided in the separate signal path of the pilot tone signal, with which a level of the pilot tone signal can be reduced to a level less than or equal to a level of the received magnetic resonance signal. The attenuator can in principle be arranged in the entire signal path of the pilot tone signal, before it is combined with the magnetic resonance signal for further processing. The attenuator is preferably arranged upstream of the frequency conversion of the pilot tone signal into the frequency range of the magnetic resonance signal, so that no high signal levels that could cause interference occur in the frequency range of the magnetic resonance signal. It is also conceivable for the attenuator to be an integral component of the above-described function groups, for example LNA 55 or first filter 56 in the signal path.

The local coil 50 in FIG. 2 furthermore has a pilot tone transmitter 70. To this end, the local coil 50 receives an oscillator signal from the magnetic resonance tomography system 1 via a signal input, from which the pilot tone and the mixed frequency are derived. The pilot tone is derived by the pilot tone transmitter 70 from the oscillator signal or is generated therefrom and is coupled out into the environment as a magnetic alternating field via the pilot tone transmission antenna or coupling loop.

An exemplary frequency scheme is explained below. A determining element for the frequency scheme is the field magnet 10, which, with the type of the nuclear spins to be detected, determines the frequency of the magnetic resonance signal, known as the Larmor frequency. For the specimen calculation, a value of 23.6 MHz is here assumed for a low field system. The oscillator signal has a nearby frequency, which however no longer lies in the frequency range or bandwidth of the magnetic resonance signal and does not interfere with the image capture. A frequency of 22.5 MHz is here assumed as a specimen value.

In a first frequency multiplier 59, the pilot tone signal is generated therefrom and is coupled out into the patient via an induction coil. A multiplication factor may for example be 5, so that the pilot tone signal has a frequency of 112.5 MHz. The mixed frequency is generated by a second frequency multiplier 60 from the oscillator signal, wherein the factor differs. For example, the factor here may be 4, so that the mixed frequency is 4*22.5 MHz=90 MHz.

Multiplications by a factor of 4 can for example be achieved with a full wave rectifier and subsequent filtering of the harmonics, while uneven harmonics can be generated by limiting/squaring.

If the pilot tone signal and the mixed signal are mixed in the mixer 57, this results inter alia in a mixed product with a frequency corresponding to the difference between the frequency of the mixed signal and of the pilot tone signal, in other words where (5−4)*22.5 MHz=22.5 MHz again to the frequency of the oscillator signal. It is also conceivable for the multiplication factor of the frequency of the mixed signal to be higher by one. However, other schemes are also possible, for example with a lower frequency of the oscillator signal, which corresponds to half the frequency equal to 11.25 MHz. Multiplication factors with a difference of 2 can then be selected, which allows the use of simple frequency multipliers with even harmonics for both signals.

The signal-to-noise ratio (SNR) of the MR signal must not be appreciably reduced by the combination with the PT received signal, for example by less than 50 mdB. It must hence be ensured, by suitable design of the pilot tone signal level from the antenna coil 51 to the combination of the magnetic resonance signal with the pilot tone signal for transmission to the magnetic resonance tomography system, that during the combination the noise floor of the PT received signal remains at least 20 dB below the noise floor of the MR received signal. This can be achieved by corresponding dimensioning of the preamplifiers and/or by the asymmetrical design of the combination, for example of the resistance values in the case of a summing element, which here assumes the function of the attenuator. The thereby increased noise figure in the pilot tone signal reception path compared to the magnetic resonance signal reception path can be compensated for by a correspondingly higher pilot tone amplitude.

Figure 3:
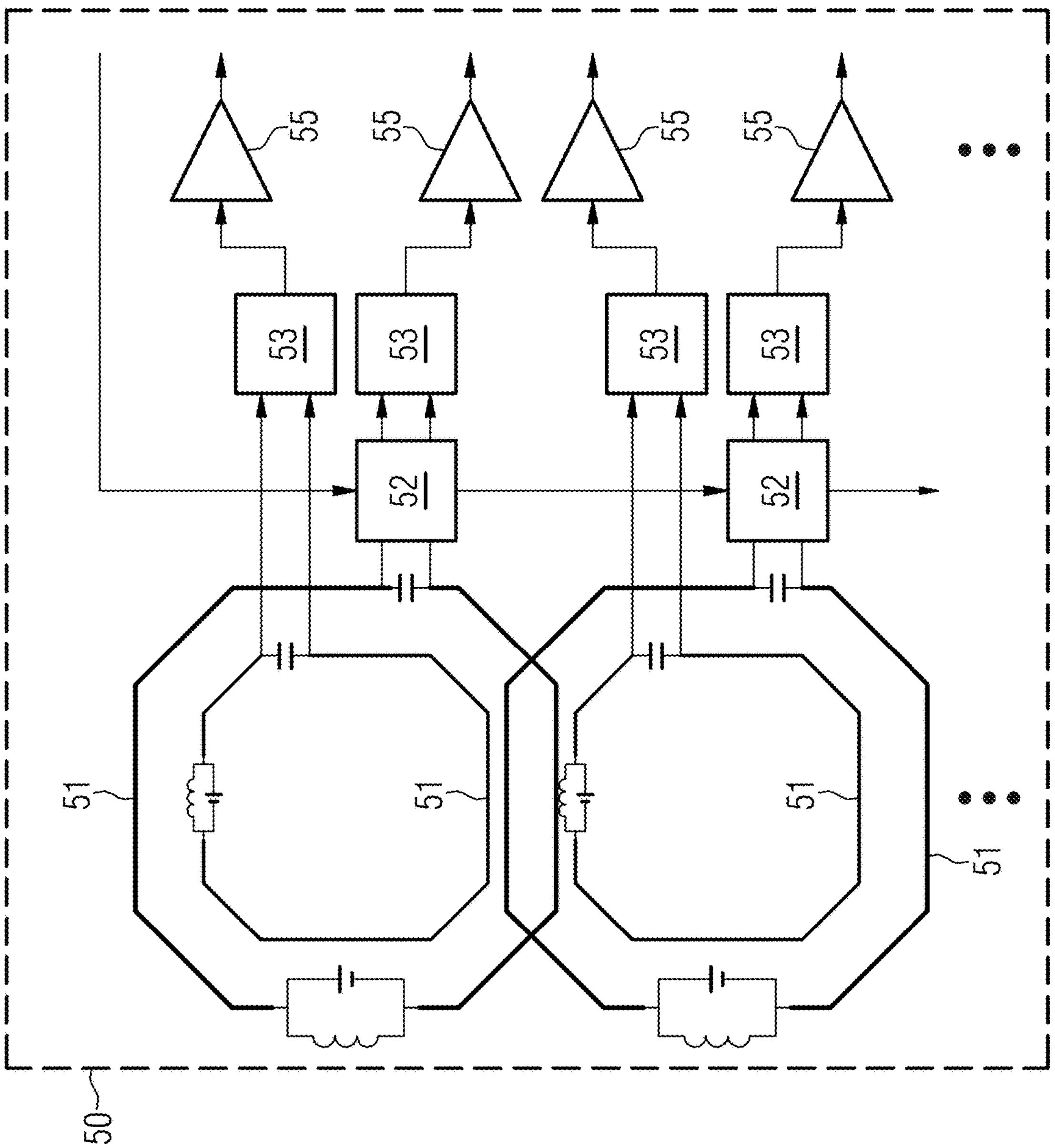
FIG. 3 shows a schematic representation of parts of an exemplary local coil.

FIG. 3 shows a schematic representation of parts of an exemplary implementation of the local coil 50. The local coil 50 in FIG. 3 differs from the implementation in FIG. 2 in that a double-resonance antenna coil 51 is not used for the receipt of both the pilot tone signal and the magnetic resonance signal, but separate antenna coils 51 in each case. Only the parts that differ from those in FIG. 2 are shown in FIG. 3.

FIG. 3 shows a total of four antenna coils 51, in each case pairs consisting of an antenna coil 51 for the pilot tone signal and an antenna coil 51 for the magnetic resonance signal, the output signals of which are forwarded together to a receiver 40 of the magnetic resonance tomography system 1. The antenna coils 51 of the pairs are arranged concentrically in FIG. 3, and although this is not absolutely essential it reduces the space requirement. An antenna coil 51 for the pilot tone signal can also be designed to be significantly smaller than the antenna coil 51 for the magnetic resonance signal. The resulting reduction in sensitivity can be compensated for by a corresponding increase in the amplitude of the pilot tone.

In the implementation in FIG. 3, only one detuning device 52 is provided in each case for the antenna coil 51 that is to receive the magnetic resonance signal. In contrast, the antenna coil 51 for the pilot tone signal can be permanently tuned to the substantially higher frequency of the pilot tone signal, so that it is excited only slightly and harmlessly by the excitation pulse. Since the signals are already physically separate, it is also possible to dispense with signal separation by a diplexer 54. The further processing of the signals takes place as shown in FIG. 3.

Figure 4:
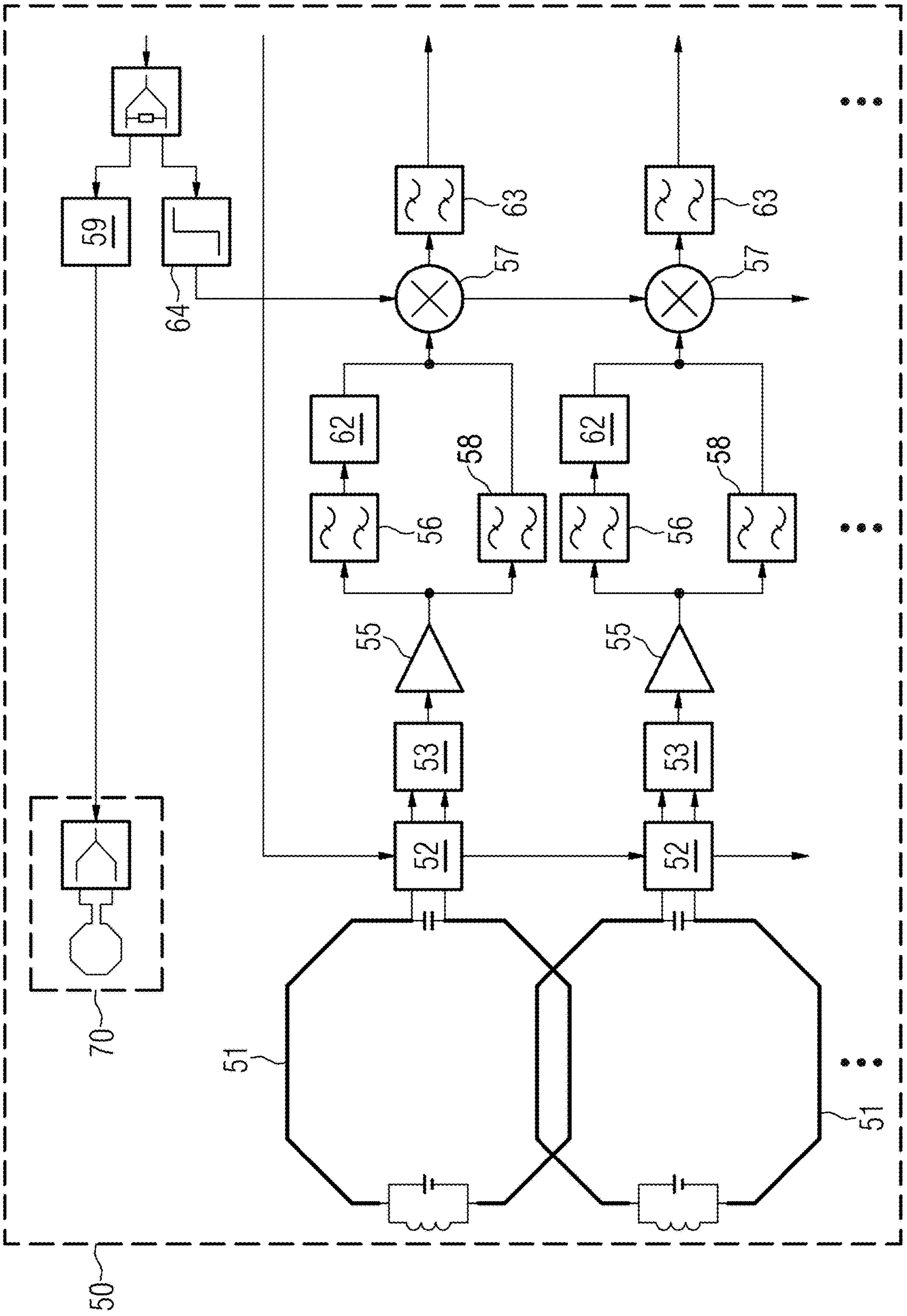
FIG. 4 shows a schematic representation of an exemplary local coil.

FIG. 4 shows a schematic representation of an exemplary implementation of a local coil 50. The local coil 50 in FIG. 4 differs from the implementation in FIG. 2 in the type of mixers 57 and the preprocessing of pilot tone signal and mixer frequency.

The mixers 57 provided in FIG. 4 are switching mixers, i.e., a signal to be mixed is not multiplied in an analog manner with a preferably sinusoidal mixed signal but is switched in polarity digitally with a mixer frequency, or is switched on and off. Due to the Fourier decomposition, this corresponds to mixing the signals to be mixed with an analog or multiplicative mixer with a bundle of sinusoidal signals with mixer frequencies with uneven harmonics of the original digital mixer signal.

As in FIG. 2, magnetic resonance signal and pilot tone signal are initially acquired with a double-resonance antenna coil 51. Detuning by the detuning device 52, matching with the matching circuit 53, and preamplification by the LNA 55 are carried out together for both signals. The signals are then separated by the first filter 56 and the second filter 58 on the basis of their frequency. The pilot tone signal can be matched in amplitude by an attenuator 62, in order, as described above, to ensure an optimal SNR for the magnetic resonance signal. The first filter 56 and the second filter 58 additionally ensure that no undesired side-frequencies are contained, which would result in interfering mixed products with interfering frequencies in the subsequent mixer.

The mixer 57 as a switching mixer means that the input signals are simultaneously mixed with different frequencies, correspondingly resulting in a plurality of mixed products. Mixed products of the pilot tone signal and of the magnetic resonance signals are selected from these with a third filter 63 in accordance with the frequency scheme in FIG. 4 explained below, lie in a common frequency range, and can be evaluated together by the subsequent receiver 40.

In the implementation in FIG. 4, the magnetic resonance signal for example lies unchanged in a frequency range around 23.6 MHz. A frequency of 35 MHz is provided for the oscillator signal in this example. From this, a signal shaper 64, for example a Schmitt trigger, generates a square-wave signal with 35 MHz as the mixer frequency for the switching mixer. A first frequency multiplier 59, here a synthesizer, generates a pilot tone signal with 117.5 MHz from the oscillator signal. A PLL with 117.5 MHz VCXO would be conceivable. The comparison frequency is selected as 2.5 MHz. For this, the VCXO signal must be divided by 47 and the 35 MHz reference signal by 14.

The switching mixer, actuated with a mixer frequency of 35 MHz, firstly generates a signal of 35 MHz−23.6 MHz=11.4 MHz with the magnetic resonance signal of 23.6 MHz.

For the pilot tone, the third harmonic of the frequency of the mixed signal is taken into account: 117.5 MHz−3*35 MHz=12.5 MHz.

After a third filter, which removes undesired other mixed products outside the common frequency range of for example 11 MHz to 13 MHz, the signal mixture is supplied to the receiver 40 for further processing.

Besides the reduced number of mixers, which additionally can still more easily be realized as switching mixers, a conversion to a lower intermediate frequency is advantageously simultaneously carried out, which reduces the attenuation on the transmission path and additionally decouples the primary magnetic resonance signal in the frequency space from the output signal.

A downstream conversion to an intermediate frequency or else multiple intermediate frequencies for a frequency multiplex is of course also conceivable for the forms of embodiment in FIGS. 2 and 3.

Although the invention has been illustrated and described in greater detail by the preferred exemplary embodiment, the invention is nevertheless not restricted by the disclosed examples and other variations can be derived therefrom by the person skilled in the art, without departing from the scope of protection of the invention.

The invention claimed is:

1. A local coil for a magnetic resonance tomography system, the local coil comprising:

the local coil configured to receive a pilot tone signal in a first frequency range and a magnetic resonance signal in a second frequency range, the first frequency range being disjunct from and having a frequency spacing from the second frequency range;

at least a first frequency converter configured to convert the pilot tone signal and the magnetic resonance signal into a common frequency range;

an input for an oscillator signal; and a circuit configured to generate from the oscillator signal a pilot tone for transmission and a mixer signal for frequency conversion of the pilot tone signal with the first frequency converter, the circuit comprising a first frequency multiplier with a first multiplication factor for generating the pilot tone from the oscillator signal and a second frequency multiplier with a second multiplication factor for generating the mixer signal from the oscillator signal, wherein the first multiplication factor and the second multiplication factor differ by the number 1.

2. A magnetic resonance tomography system comprising:

an oscillator;

a local coil configured to receive an oscillator signal from the oscillator and generate a pilot tone, the local coil comprising:

a frequency converter configured to convert a pilot tone signal and a magnetic resonance signal received by the local coil into a common frequency range, an input for the oscillator signal, and a circuit configured to generate from the oscillator signal the pilot tone for transmission and a mixer signal for frequency conversion of the pilot tone signal with the first frequency converter, the circuit comprising a first frequency multiplier with a first multiplication factor for generating the pilot tone from the oscillator signal and a second frequency multiplier with a second multiplication factor for generating the mixer signal from the oscillator signal; and a receiver configured to receive the magnetic resonance signal and the pilot tone signal, wherein the first multiplication factor and the second multiplication factor differ by the number 1.

3. The local coil of claim 1, wherein the mixer signal has the same frequency as the oscillator signal and the first frequency converter is a switching mixer.

4. The local coil of claim 1, further comprising an antenna coil that simultaneously has a resonance in the first frequency range and the second frequency range.

5. The local coil of claim 1, further comprising an attenuator configured to attenuate the pilot tone signal to a level equal to or less than the magnetic resonance signal to be received, before being output by the local coil.

6. The local coil of claim 1, further comprising a transmitter configured to transmit the pilot tone with a level which results in a level of the received pilot tone signal that is higher than the magnetic resonance signal to be received.

7. The magnetic resonance tomography system of claim 2, wherein the local coil comprises an antenna coil configured to receive the pilot tone signal in a first frequency range and a magnetic resonance signal in a second frequency range, the first frequency range being disjunct from and having a frequency spacing from the second frequency range.

8. The magnetic resonance tomography system of claim 2, wherein the mixer signal has the same frequency as the oscillator signal and the first frequency converter is a switching mixer.

9. The magnetic resonance tomography system of claim 2, wherein the local coil comprises an attenuator configured to attenuate the pilot tone signal to a level equal to or less than the magnetic resonance signal to be received, before being output by the local coil.

10. The local coil of claim 1, further comprising a mixer configured to mix the pilot tone signal and the mixer signal, such that a mixed product is generated, wherein the mixed product comprises a mixed frequency corresponding to an absolute value of a difference between a frequency of the mixer signal and a frequency of the pilot tone.

11. The magnetic resonance tomography system of claim 2, further comprising a mixer configured to mix the pilot tone and the mixer signal, such that a mixed product is generated, wherein the mixed product comprises a mixed frequency corresponding to an absolute value of a difference between a frequency of the mixer signal and a frequency of the pilot tone.

12. The magnetic resonance tomography system of claim 2, wherein a frequency corresponding to an absolute value of a difference between a frequency of the mixer signal and a frequency of the pilot tone is the same as a frequency of the oscillator signal.

13. The local coil of claim 3, further comprising an antenna coil that simultaneously has a resonance in the first frequency range and the second frequency range.

14. The local coil of claim 5, further comprising multiple antenna coils, and wherein the attenuator is one of multiple attenuators assigned to the multiple antenna coils, wherein an attenuation value differs for at least two attenuators.

15. The local coil of claim 10, wherein the mixed frequency corresponding to the absolute value of the difference between the frequency of the mixer signal and the frequency of the pilot tone is the same as a frequency of the oscillator signal.

16. The local coil of claim 13, further comprising an attenuator configured to attenuate the pilot tone signal to a level equal to or less than the magnetic resonance signal to be received, before being output by the local coil.

17. The local coil of claim 16, further comprising a transmitter configured to transmit the pilot tone with a level which results in a level of the received pilot tone signal that is higher than the magnetic resonance signal to be received.

* * * * *